United States Patent [19]

Katschnig et al.

[11] Patent Number: 5,098,665

[45] Date of Patent: Mar. 24, 1992

[54] DEVICE FOR HEATING OF ARTICLES AND ORGANISMS

[75] Inventors: Helmut Katschnig, Burggasse 108, Judenburg, Austria, A-8750; Wolfgang Moøshammer, Judenburg, Austria; Christian Bischoff, Judenburg, Austria; Erwin Berger, Judenburg, Austria

[73] Assignee: Helmut Katschnig, Judenburg, Austria

[21] Appl. No.: 180,422

[22] Filed: Apr. 12, 1988

[30] Foreign Application Priority Data

Apr. 14, 1987 [AT] Austria .................................. 932/87

[51] Int. Cl.[5] .............................................. A61L 2/12
[52] U.S. Cl. ...................... 422/108; 422/113; 422/117; 422/119; 422/21; 422/307; 219/10.55 D; 219/10.55 F
[58] Field of Search .............. 422/2, 21, 28, 105, 422/112, 113, 117, 307, 119, 108, 186, 186.04; 219/10.55 R, 10.55 D, 10.55 F, 10.55 A

[56] References Cited

U.S. PATENT DOCUMENTS

| | | | |
|---|---|---|---|
| 2,550,584 | 4/1951 | Mittelmann | 219/39 |
| 2,593,067 | 4/1952 | Spencer | 219/47 |
| 3,402,277 | 9/1968 | Muller | 219/10.55 |
| 3,436,508 | 4/1969 | Fritz | 219/10.55 |
| 3,651,300 | 3/1972 | Haagensen | 219/10.55 |
| 3,753,651 | 8/1973 | Boucher | 422/21 |
| 3,916,137 | 10/1975 | Jurgensen | 219/10.55 A |
| 4,004,122 | 1/1977 | Hallier | 219/10.55 |
| 4,032,910 | 6/1977 | Hollway et al. | 340/600 |
| 4,144,436 | 3/1979 | Hauck | 219/10.55 F |
| 4,253,092 | 2/1981 | Connah | 340/539 |
| 4,321,577 | 3/1982 | Carlson | 422/98 X |
| 4,400,357 | 8/1983 | Hohmann | 422/297 |
| 4,411,866 | 10/1983 | Kanno | 422/25 |
| 4,417,116 | 11/1983 | Black | 219/10.55 |
| 4,599,216 | 7/1986 | Rohrer et al. | 422/21 |
| 4,771,156 | 9/1988 | Strattan et al. | 219/10.55 M |
| 4,896,010 | 1/1990 | O'Connor et al. | 422/21 |

FOREIGN PATENT DOCUMENTS

| | | |
|---|---|---|
| 1190605 | 7/1985 | Canada . |
| 0047356 | 3/1982 | European Pat. Off. . |
| 0051569 | 5/1982 | European Pat. Off. . |
| 0069105 | 1/1983 | European Pat. Off. . |
| 0107270 | 5/1984 | European Pat. Off. . |
| 0116921 | 8/1984 | European Pat. Off. . |
| 0198430 | 10/1986 | European Pat. Off. . |
| 3430673 | 2/1986 | Fed. Rep. of Germany . |
| 3505571 | 8/1986 | Fed. Rep. of Germany . |
| 2073337 | 10/1971 | France . |
| 2250254 | 5/1975 | France . |
| 2455463 | 11/1980 | France . |
| 8204188 | 12/1982 | PCT Int'l Appl. . |
| 8602842 | 5/1986 | PCT Int'l Appl. . |
| 8604206 | 7/1986 | PCT Int'l Appl. . |
| 1292730 | 10/1972 | United Kingdom . |

Primary Examiner—Robert J. Hill, Jr.
Assistant Examiner—Jeffrey R. Snay
Attorney, Agent, or Firm—Pennie & Edmonds

[57] ABSTRACT

A device is disclosed for heating of articles and organisms, and in particular for destroying or rendering harmless organisms containing nucleic acids and/or proteins by action of microwave radiation generated by a microwave emission device. The microwave emission device illustratively comprises a plurality of magnetrons emitting microwave radiation into a sterilization chamber and configured such that cold spots are avoided. The invention further relates to a microwave radiation level monitoring device positioned in the vicinity of areas of likely microwave leakage such as a door to the sterilization chamber.

20 Claims, 2 Drawing Sheets

Section A-A

Section B-B

Section A-A

Section B-B

DEVICE FOR HEATING OF ARTICLES AND ORGANISMS

BACKGROUND OF THE INVENTION

This relates generally to a device for heating articles and organisms and in particular to a device for rendering harmless or destroying organisms containing nucleic acids and/or proteins by transmission of microwaves radiation into a chamber containing the articles and/or organisms wherein such radiation is generated by a plurality of magnetrons configured to avoid cold spots.

It is known that living cells and organisms as well as small viruses and other organisms containing proteins and nucleic acids can be destroyed or rendered harmless by the action of chemical or physical substances, whereby they lose their toxicity. Infected material may be sterilized by physical methods, such as exposure to heat, radiation (beta rays, X-rays, gamma rays, UV radiation) chemical methods and special filtration, in which the organisms are physically retained. Exposure to a sufficient amount of heat for a sufficient time irreversibly damages and renders harmless the proteins and/or nucleic acid contained within the infected material. Thus, all growth and reproductive functions of the organism exposed to such heat are destroyed. Devices for exposing material to heat for sterilization purposes are presently routinely used worldwide in the medical and industrial fields. Such devices are also frequently employed for destroying a wide variety of infectious waste prior to final disposal and for preventing harm to disposal personnel as well as to the general public.

Known devices which expose infected material to heat typically operate either by the method of hot air sterilization or by autoclaving. In these methods, heat (hot air sterilization), or steam under pressure (autoclaving) must be supplied from an external environment to the infected material to be sterilized, so that successful sterilization may only be attained by precisely following exacting procedures.

Although these two methods of heat sterilization are generally considered reliable and result in relatively complete sterilization of the infected material, an enormously high outlay of energy and time is required in order to adequately sterilize the infected material. Furthermore, a most unpleasant and unavoidable odor is generally produced by these methods.

Exposure of the infected material to radiation, and in particular to radioactivity, may render the infected material harmless but is hardly practicable for sterilization of infected material because of high industrial and safety engineering costs associated with use of sufficiently radioactive substances.

Filtration of the infected material, in which the organisms must be physically collected in a filter in especially high concentration is not a complete nor adequate solution as the collected organisms must still be disposed of. Apart from this, the method is largely limited to liquids, and possibly gases, but cannot be employed for organisms found on solid carriers.

In addition to these methods and devices, chemical methods in which disinfectant chemicals are employed for sterilizing infected material may be used. However, chemical methods are suitable primarily for surface disinfection and for disinfecting of interior walls of hollow chambers into which the disinfectants can be introduced in a controlled manner.

A final method of destroying or rendering harmless organisms containing nucleic acids and/or proteins comprises exposing such organisms or articles infected with such organisms to microwave radiation.

Living structures exposed to microwave radiation undergo a heating of fluids from within the structure, such heating exceeding the boiling point of the fluids and resulting in death or destruction of the organism. A requirement of microwave sterilization is that all organisms present in the sterilization chamber be exposed to sufficient microwave energy. In conventional devices, precautions have not been taken to avoid the occurrence of the so-called "cold spots." The avoidance of such cold spots is essential when infected articles are placed in the sterilization chamber to be uniformly exposed to microwave radiation and thus sterilized. Since the microwave radiation is transmitted for a relatively short time only, any heating by heat conduction in the infected material itself is without practical significance and will not significantly aid in the sterilization of the material.

In addition to problems associated with supplying inadequate microwave radiation to certain areas of the sterilization chamber, known microwave devices often leak microwave radiation to the environment external to the device.

More particularly, known microwave devices will in general exhibit scattering radiation, i.e. a portion of the high frequency radiation generated by the device will leave the system at points not completely impervious to high frequency radiation. Most of this leakage radiation is typically given off through door crevices and seals. Furthermore, such leakage radiation is not limited to microwave devices for performing sterilization but exists in practically all microwave generating devices.

The high-frequency leakage radiation represents a potential hazard to the operator of the device as well as others in close vicinity. For this reason, there are internationally set standards on maximum allowable peak limits of radiation emitted from microwave devices. Thus a device when sold must not emit to the environment more than a prescribed output density of microwave radiation.

It is known, however, that leakage of microwave radiation may be minimized through utilization of suitable materials and constructing the device in accordance with proper specification. However, regardless of the quality of materials or construction or even the initial minimization of microwave radiation, the materials and components constructed therefrom are all subject to aging and/or wear resulting in increased microwave radiation leakage. Moreover, such increased microwave leakage typically occurs without the knowledge of the operator, thereby potentially exposing the operator or other personnel to increasingly severe levels of radiation resulting in irreversible harm.

In particular, known devices and methods exist whereby the amount of leakage of microwave radiation may be tested. Unfortunately, such devices are not generally available to the operator, nor are there generally any statutory provisions calling for periodic inspection of a microwave device including measurement of leakage radiation. Furthermore, the cost of such an output density measuring system is often prohibitive and thus such devices are generally not owned by most microwave device owners. Even if microwave devices are repeatedly subjected to testing, during operation of the device, such as in the period between two successive tests, the operator can have no complete assurance that prior leakage levels accurately reflect present microwave leakage levels. For example, rubber gaskets may become damaged and indeed do generally degrade with time. Such damage may not become apparent until the next inspection of the device. In the interval, the operator of the device would have been exposed to the microwave radiation without protection.

Illustrative of prior art sterilization methods is German Patent 3430673 which discloses a sterilization process in which the material to be sterilized is passed through a hollow conductor between two synchronously running conveyor belts. Unfortunately, what is generally referred to as "cold spots", i.e., portions of the hollow conductor not receiving sufficient sterilizing radiation, are often developed in such a hollow conductor. Such cold spots prevent complete sterilization of the material in practice and lead to an increased risk of infection and the like. Furthermore, this device is complicated in structure and involves problems associated with shielding the outside environment from the microwave radiation.

European Patent Application 0 116 921 discloses a sterilization system for infusion of a liquid from an external closed container into a patient. More specifically, the external closed container is provided with a first conduit connected to a coupling which is also connected to the patient by way of a second conduit. A small volume of liquid is permitted to flow to the coupling whereupon a guided wave member is then placed over the coupling and emits radiation to destroy any bacteria present in the coupling. Unfortunately, this device is limited to sterilizing liquid contained within a coupling connecting two conduits. It is often desirable to sterilize other materials and in fact it is generally necessary to sterilize medical wastes in order to destroy organisms such as bacteria, viruses and spores contained therein. However, known devices and methods are not capable of adequately disinfecting or sterilizing medical waste and the like prior to disposal in a land fill or combustion facility so as to avoid endangering disposal personnel as well as the general public.

U.S. Pat. No. 2,550,584 discloses a milk pasteurization system in which milk continuously flows through a heat exchanger and through a fluid cooled high frequency electronic tube heater. The high frequency heater comprises a cylindrical member having an input end and an output end. Heat from the high frequency heater is used to preheat the milk in the heat exchanger. However, this device is limited to pasteurizing milk.

SUMMARY OF THE INVENTION

The present invention comprises a sterilization chamber and a plurality of microwave emitting means configured so as to avoid so-called cold spots, thereby providing for reliable sterilization of the entire infected material present in the sterilization chamber. Advantageously, the microwave emitting means preferably comprises a plurality of microwave emitting devices configured such that any one of the microwave emitting devices radiates into a space defined by the sterilization chamber free from microwaves emitted from the other microwave emitting devices. As a result, it is ensured that no cold spots will form in the sterilization chamber.

The present invention is thus especially suitable for sterilizing medical appliances, for sterilizing infectious medical waste to be properly disposed and for sterilizing surgical linen or dressing materials. In addition, liquids or gases continuously passing through hoses in the sterilization chamber may also be sterilized.

In a preferred embodiment of the invention, three microwave emitting devices are provided, two of which are located in one side wall of the sterilization chamber and the third is located in a wall of the sterilization chamber opposite to the one side wall. This arrangement of the microwave emitting devices is especially advantageous in the avoidance of cold spots.

The microwave emitting devices which supply microwave radiation to the interior of the sterilization chamber generate heat during typical use. Thus, a cooling arrangement is desirable. The microwave emitting devices of the present invention are advantageously arranged outside of the sterilization chamber in a cooling chamber capable of being ventilated by way of cooling fans which are readily accessible to inspection.

Cooling fans may also be utilized for circulation of air in the interior of the sterilization chamber. This is accomplished by openings near a floor member of the sterilization chamber, such openings providing air flow between the cooling chamber(s) and the sterilization chamber.

The electrical field strength E-vectors of the microwave radiation emitted by the magnetrons are oriented orthogonally or approximately orthhogonally with respect to each other, the direction of each of these three E-vectors of the microwaves being offset from the direction of the axes of the cartesian coordinate system formed by the three mutually perpendicular edges of the rectangular sterilization chamber. The three magnetrons and their configuration ensure an output density uniformly distributed over the interior of the sterilization chamber, thus enabling the infected material to be uniformly and completely sterilized.

The present invention advantageously includes a thermal relay associated with the sterilization chamber for protection against overheating. It is thus ensured that neither the equipment nor the articles placed in it will suffer heat damage, since the heat will act only to destroy the organisms. Furthermore, if steam is generated in the sterilization chamber, a safety valve is preferably provided from the interior of the sterilization chamber to exhaust excessive pressure and render the sterilization chamber safe from excessive internal pressure. Destruction of the sterilization chamber and associated equipment accompanied by the emergence of potentially harmful organisms, as well as emission of microwave radiation into the surrounding space is thus advantageously prevented.

In a further embodiment of the invention, a flap valve is provided in a wall of the sterilization chamber and serves as an outlet passage from the interior of the sterilization chamber to an exhaust duct preferably opening into a sewer system. In this way, all fumes and odors arising in the course of sterilization can be carried off, preferably into the sewer system, so that there will be no objectionable odors creating a nuisance or hazard to operating personnel or the surroundings.

The present invention preferably includes means to measure the sterilizability of material, such means comprising a test passage leading from the interior of the sterilization chamber to the exterior, a suction fan for aspirating air from the interior of the sterilization chamber, heating means for heating the aspirated air to a predetermined temperature and a humidity sensor to determine the humidity level of the heated air. The heating means and the humidity sensor may be positioned within the test passage.

This configuration advantageously permits measurement of the atmospheric humidity in the sterilization chamber continuously during the sterilization process and thus enables one to determine whether particular material is sterilizable and operate the device accordingly. Material not sterilizable by way of microwave radiation, for example, dry material, can easily and automatically be identified as such. More specifically, as soon as the moisture content rises to a value significantly different from the initial moisture content prior to energization of the microwave emitter means, it may be concluded that the material to be sterilized has attained at least the boiling temperature of water. Thus it is possible to automatically determine whether any sterilizable material is present in the sterilization chamber. If the heating means and humidity sensor are arranged in the test passage, a compact design results which advantageously permits determining moisture content at its place of origin, as close as possible to the interior of the sterilization chamber.

The test passage employed for determining moisture content preferably opens into the exhaust duct which leads into a sewer system or the like. Thus it is ensured that even the small quantity of air from the interior of the sterilization chamber that is required for determination of the humidity from time to time will not leak into the air surrounding the sterilization system.

The humidity sensor is preferably coupled to a means for shutting off the energy supply of the microwave emitting means. It is thereby possible to switch the device off when the material contained in it is not sterilizable by way of microwave radiation. In the presence of sterilizable material in the sterilization chamber, the humidity sensor should register a rise in humidity after the system has been started and microwave radiation emitted. If no such rise is registered, the device switches off. A visible and/or audible indicating means is preferably provided with the present invention to automatically indicate that non-sterilizable material is present in the sterilization chamber.

In addition to the sterilization of infected material by microwaves, an independent source of liquid may be arranged in the interior of the sterilization chamber, such as a receptacle filled with water and/or disinfectants and/or deodorants. The receptacle for the liquid need not be sealed and preferably exposes the liquid which vaporizes during operation of the device, thereby disinfecting, deodorizing or further heating the infected material.

In a further embodiment of the invention, microwave radiation leakage is advantageously continuously monitored so that in case of excessive leakage steps may immediately be taken for the safety of the operator as well as others in the environment. This is accomplished by protection and/or monitoring means located in the regions of typical areas of leakage such as a door. Additionally, such means may be located for monitoring microwave radiation levels in or within the vicinity of test passages, valves and the like. Preferably, the perimeter of any opening or potential source of leakage is lined with an antenna fitted to the opening. This arrangement permits constant monitoring of the opening for detecting the leakage of hazardous microwave radiation. Advantageously, such an arrangement may be applied to any microwave emitting means, independently of the number of individual microwave emitting devices including, for example, so-called microwave ovens, widely employed in households and commercial food establishments for the heating and/or cooking of food.

Signals received by and transmitted along the antenna, illustratively a wire loop, are supplied to a threshold detection circuit to determine whether the radiation received by the antenna is greater than a maximum prescribed safety limit of radiation. The threshold detection circuit is preferably coupled to a shut-off means for disconnecting the electric supply from the microwave emitting means. Additionally, a visual or audible signal may be provided to indicate surpassion of the threshold value thereby warning personnel of a potentially hazardous situation and enabling proper precautions to be taken. In this way it can be ensured that when the threshold value (which should be close to the allowable dosage limit) is reached, a visual or audible alarm signal will be produced, and/or the device will be automatically switched off.

The antenna is preferably arranged on a perimeter of a frame around the opening in the region of scattered radiation potentially passing through cracks, crevices or areas partially transparent to microwave radiation. The antenna is connected to a diode which rectifies the AC signal present on the antenna. A comparator circuit compares the voltage after the diode to a predetermined voltage corresponding to the maximum prescribed safety limit of radiation, i.e. the threshold voltage. If the rectified voltage exceeds the threshold voltage, the visual and/or audible alarm will be activated.

BRIEF DESCRIPTION OF THE DRAWINGS

These and other objects, features and advantages of the invention will be more readily apparent from the following detailed description of the drawings in which.

DETAILED DESCRIPTION OF THE PREFERRED EMBODIMENT

Figure 1:
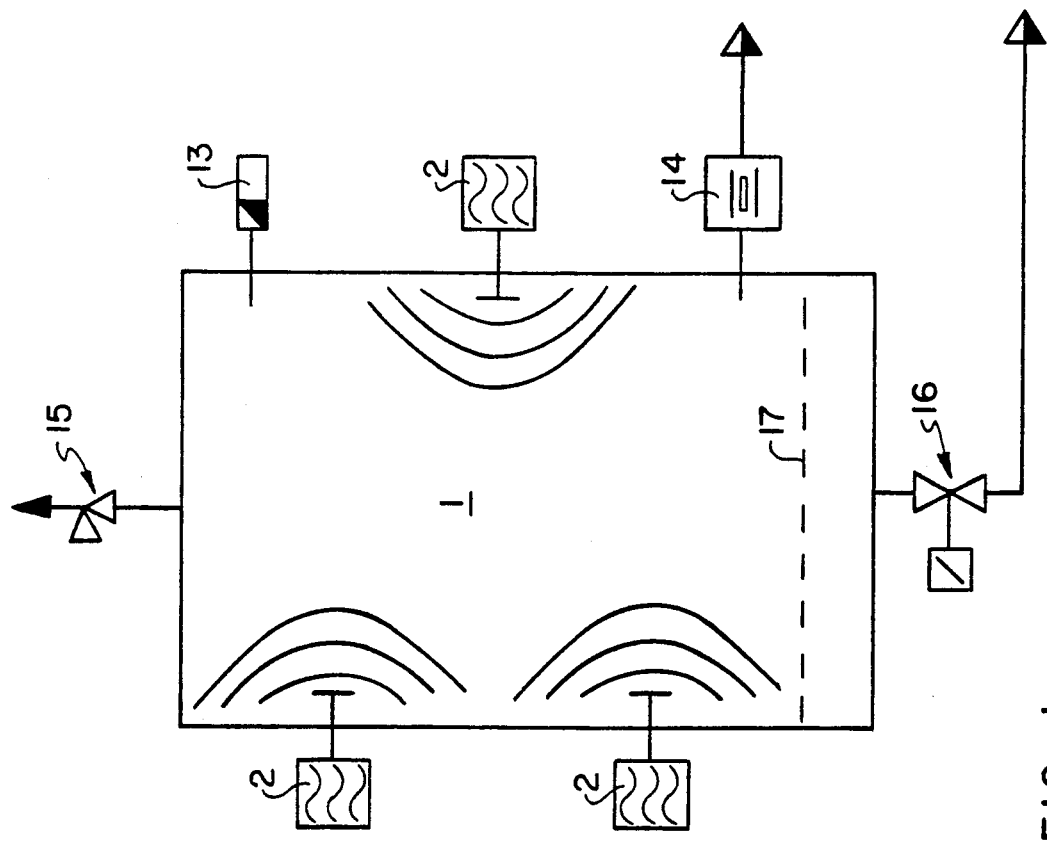
FIG. 1 depicts a front view of a first embodiment of the invention.

Referring initially to FIG. 1, a device for heating articles and organisms comprises a heating cavity 1, a plurality of microwave emitting means 2, thermal relay 13, atomizer 14, pressure relief valve 15 and drain valve 16.

Heating cavity 1 may take on a wide variety of forms and preferably is an approximately rectangular sterilization chamber having four side walls, a ceiling member and a floor member. Sterilization chamber 1 is provided with an opening (not shown) for insertion and removal of material to be sterilized. The opening preferably is through one of the side walls and is closable by way of a door member. Such a closable structure is well known in the art and need not be detailed further.

Microwave emitting means 2 may also take on a wide variety of forms. Illustratively, microwave emitting means 2 is a magnetron or, alternatively, a klystron. Microwave emitting means 2, upon application of an electric power supply, emits high frequency radiation, and more specifically, microwave radiation, into sterilization chamber 1 for heating material therein. Microwave emitting means 2 preferably comprises three magnetrons each of which emits microwave radiation into the interior space defined by sterilization chamber 1. Magnetrons 2 are physically arranged with respect to each other and with respect to the sterilization chamber such that they emit radiation which uniformly sweeps and fills sterilization chamber 1 thereby preventing cold spots. Such a physical arrangement of the magnetrons advantageously permits infected material and the like which is enclosed by the sterilization chamber to be wholly exposed to a sufficient amount of microwave radiation so as to completely sterilize the infected material contained therein.

The effectiveness of the microwave radiation in sterilizing the infected material is preferably increased by introducing cold water vapor into the sterilization chamber. Such cold water vapor is generated by an external atomizer 14, illustratively an ultrasonic atomizer which introduces the cold water vapor into the sterilization chamber for subsequent heating by the magnetrons. The cold water vapor is heated and increases the temperature to which the infected material is exposed thereby increasing the efficiency and effectiveness of the sterilization process.

Pressure relief valve 15 provides a conduit from the interior of sterilization chamber 1 to the exterior environment upon an increase in pressure within the sterilization chamber beyond a tolerable limit.

Thermal relay 13 is also preferably provided as protection against overheating and shuts off the power supply to the magnetrons in the event of excessive temperature. Either or both of pressure relief valve 15 and thermal relay 13 may shut off the magnetron and/or provide a visual and/or audible alarm to an operator to indicate that excessive pressure or temperature has been reached.

Drain valve 16 is provided at the bottom of sterilization chamber 1 for the removal of liquid waste, condensed steam and to facilitate cleaning of the chamber. The entire sterilization process may be controlled by way of an electronic control unit (not shown). A grating 17 is preferably provided above the floor member of the sterilization chamber on which a receptacle containing the infected material to be sterilized may be placed.

Figure 2:
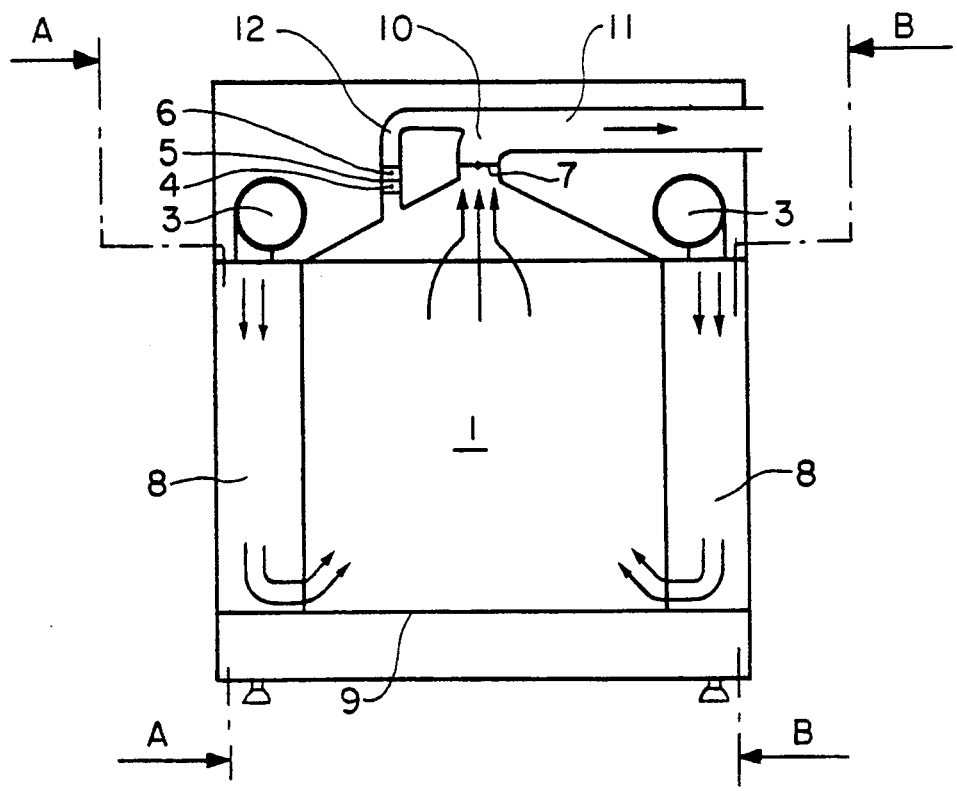
FIG. 2 depicts a front view of a second embodiment of the invention.
Figure 3A:
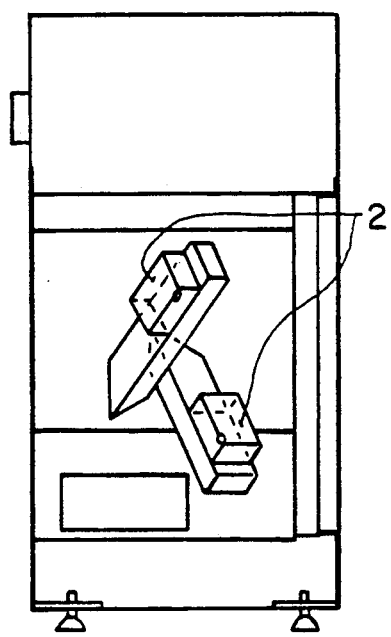
FIGS. 3A and 3B depict sections at lines A—A and B—B, respectively in the second embodiment shown in FIG. 2.
Figure 3B:
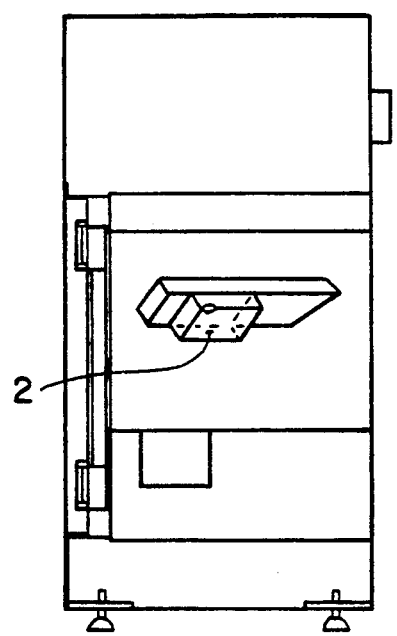

Referring now to FIGS. 2 and 3, there is depicted another embodiment of the invention in which similar elements are labelled similiarly. Microwave emitting means 2 comprises, illustratively, three magnetrons arranged on the side walls at an angle alpha, illustratively 45°, in the top view of FIG. 3 and at an angle beta, illustratively 65°, from the vertical in the front view of FIG. 2. Any suitable angles which result in the uniform emission of microwave radiation throughout the interior of sterilization chamber 1 may be utilized. As will be apparent, the electrical field strength vectors E of the microwave radiation emitted by the magnetrons are oriented orthogonally or approximately orthogonally with respect to each other, the direction of each of these three E-vectors of the microwaves being offset from the direction of the axes of the cartesian coordinate system formed by the three mutually perpendicular edges of the rectangular sterilization chamber. The three magnetrons 2 ensure an output density uniformly distributed over the interior of the sterilization chamber 1, thus enabling the infected material to be uniformly and completely sterilized. The three magnetrons are mounted within enclosed chambers 8 and are cooled by fans 3. Fans 3 also perform the function of circulating air through the interior of the sterilization chamber as shown in FIG. 2, so that the water vapor formed in the interior may be expelled. The fans 3 discharge into cooling chambers 8 in which the magnetrons are located. Cooling chambers 8 communicate with the interior of the sterilization chamber by way of openings located near a floor member 9 of the sterilization chamber. Furthermore, the interior of the sterilization chamber is connectable by way of a flap valve 7 located in an outlet passage 10 of the sterilization chamber into an exhaust duct opening and then into a sewer system. If the flap valve 7 is open, the air delivered into the sterilization chamber by fans 3 may be vented to the sewer system by way of the outlet passage 10 and exhaust duct 11.

Further, a test passage 12 is provided to communicate with the interior of the sterilization chamber. This test passage 12 can be supplied with air from the interior of the sterilization chamber by means of a small suction fan 4. The test passage 12 carries the air from the interior of the sterilization chamber through a heating means 5 and a humidity sensor 6. The heating means 5 and the humidity sensor 6 in the embodiment depicted in FIG. 2 are located in the test passage 12. The air entering the test passage 12 by suction fan 4 is thus preheated to a constant predetermined temperature by the heating means 5 and its humidity level determined by humidity sensor 6. The test passage 12 then opens into the exhaust passage 11, so that air removed from the interior of the sterilization chamber for test purposes and the like will also enter into the exhaust duct 11.

The humidity sensor 6 may be coupled, in a known manner not shown, with means for shutting off the power supply to magnetrons 2 as well as means for providing visual and/or audible indication of humidity level below a threshold level. The power supply to the magnetrons is advantageously shut off if the humidity sensor does not detect a significant increase in humidity after a predetermined amount of time as would be the situation if dry material were to be placed in the sterilization chamber and attempted to be sterilized.

In addition, the interior of the sterilization chamber 1 may be provided with a source of liquid independent of any outside supply, for example, a recepticle or bag filled with water, disinfectants or deodorants.

In operation of the device depicted in FIGS. 2 and 3, the material to be sterilized is placed in the interior of the sterilization chamber with the door open, in a receptacle transparent to microwave radiation and which is not sealed. At the beginning of the sterilizing operation, fans 3 are switched on and valve 7 is opened. By way of the small fan 4, air is removed from the interior of the sterilization chamber and heated to the predetermined constant temperature by heating means 5, and its moisture content determined at that predetermined temperature by humidity sensor 6. The valve 7 is then closed, and the magnetrons 2 are switched on. The small fan 4 continuously withdraws a certain flow of air from the interior of the sterilization chamber and its humidity is measured at constant temperature. As soon as the moisture content rises to a value differing significantly from the initial moisture content before the magnetrons 2 were switched on, it may be concluded from this rise that the material to be sterilized has reached at least the boiling temperature of water. This makes it possible to determine whether any sterilizable material is present inside the sterilization chamber. The microwave radiation is now allowed to act on the infected material for a predetermined period of time, so as to ensure destroying the organisms through sterilization. In the last phase of this sterilization process, the valve 7 is opened again, so that the moisture formed in the interior of the sterilization chamber may be blown out. The magnetrons 2 are switched off and the two fans 3 are allowed to continue in operation for a time to blow the residual moisture out of the interior of the sterilization chamber and to continue cooling the magnetrons. The door of the sterilization chamber can then be opened and the sterilized material as well as the recepticle may be removed from the sterilization chamber. If no significant rise in humidity is observed during the emission of the microwave radiation, the magnetrons 2 will be shut off after a predetermined time period, indicating that no material sterilizable by microwave radiation is present.

Figure 4:
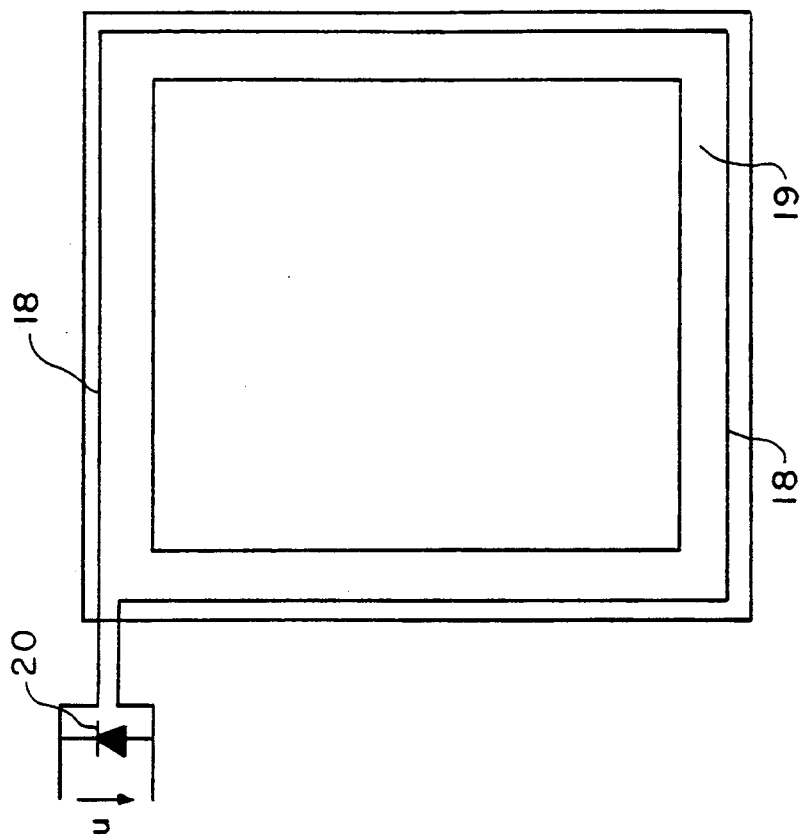
FIG. 4 depicts means for protecting and/or monitoring microwave radiation leakage in the region of a door of a microwave emitting unit.

FIG. 4 depicts a means for monitoring the level of microwave radiation leakage and is positioned in the vicinity of the closure member, i.e., the door. This monitoring means indicates when a threshold level of radiation has leaked from the sterilization chamber. Such a monitoring means may be provided for microwave emission devices in general, and is not limited to microwave devices serving to sterilize infected material. The perimeter of the sterilization chamber opening as indicated in FIG. 4 is lined in its entirety by an antenna 18 fitted to the opening. This antenna 18 is fixedly connected to a frame 19 surrounding the opening. The antenna is thus located in the region of the scattered radiation passing through the crack of the door.

The antenna is connected to a demodulator, i.e., rectifying, diode 20. The voltage U across the rectifier diode 20 is input to a comparator means (not shown). This comparator means is also input with a predetermined voltage level which corresponds to a threshold microwave radiation level beyond which it is desired to signal an alarm or shut off the magnetrons. The comparator means outputs an alarm signal if an excessive amount of radiation is detected, preferably shutting off the power supply to the magnetrons and/or providing a visual or audible signal. This visual or audible signal indicates that the threshold value has been exceeded. The monitoring means thus serves to monitor the amount of microwave radiation leakage associated with potential areas of leakage such as the door and may be employed for any microwave device such as those typically employed in households, institutional kitchens as well as microwave devices for special applications.

We claim:

1. An apparatus for sterilizing infected material comprising a sterilization chamber adapted to receive infected material to be sterilized and a microwave emitting means for emitting microwave radiation into an interior cavity defined by said sterilization chamber wherein said microwave emitting means is arranged so as to uniformly expose the interior cavity of said sterilization chamber to microwave radiation; and wherein said sterilization chamber is approximately rectangular shaped and said microwave emitting means comprises three microwave emitting devices two of which are located on one side wall of said sterilization chamber and a third microwave emitting device which is located on a wall of said sterilization chamber opposite said one side wall, said three devices being configured such that any one of said microwave emitting devices radiates into said interior cavity defined by said sterilization chamber free from microwaves emitted from the other microwave emitting devices; and wherein electrical field strength E-vectors of microwave radiation emitted by each of said three microwave emitting devices are oriented approximately orthogonal to each other, and the direction of each of said three E-vectors of the microwave radiation deviates from the direction of each of the axes defined by three adjacent edges of said approximately rectangular sterilization chamber.

2. The apparatus according to claim 1, further comprising an outlet passage communicating with the interior of said sterilization chamber for removal of air from said sterilization chamber and a flap valve in said outlet passage for regulating the removal of air.

3. The apparatus according to claim 1 further comprising a source of disinfectant liquid located in the interior of said sterilization chamber for providing a disinfectant.

4. The apparatus according to claim 1, further comprising a thermal relay arranged so as to monitor the temperature within said sterilization chamber.

5. The apparatus according to claim 4 further comprising means for shutting off an electrical power supply to said microwave emitting devices, wherein said means for shutting off is connected to and activated by said thermal relay.

6. The apparatus according to claim 1, further comprising a pressure relief valve located in said sterilization chamber for relieving excessive pressure within said sterilization chamber.

7. The apparatus according to claim 6 further comprising means for shutting off an electrical power supply to said microwave emitting devices, wherein said means for shutting off is connected to and activated by said pressure relief valve.

8. The apparatus according to claim 1, wherein each of said three microwave emitting devices comprises a magnetron and is positioned outside said sterilization chamber in a cooling chamber in flow communication with at least one fan.

9. The apparatus according to claim 8, wherein said cooling chamber is provided with a plurality of openings which communicate with the interior of said sterilization chamber.

10. The apparatus according to claim 1, further comprising a test passage communicating with the interior of said sterilization chamber, a suction fan in flow communication with said test passage for removing air from the interior of said sterilization chamber through said test passage, a heating means for heating the removed air and a humidity sensor arranged so to measure the humidity of the heated air.

11. The apparatus according to claim 10, wherein said heating means and said humidity sensor are installed within said test passage and said test passage opens into an exhaust duct.

12. The apparatus according to claim 10, further comprising means for shutting off an electrical power supply to said microwave emitting devices, wherein said means for shutting off is connected to and activated by said humidity sensor.

13. The apparatus according to claim 1, further comprising means for monitoring microwave radiation leakage from said sterilization chamber.

14. The apparatus according to claim 13, wherein said monitoring means comprises an antenna.

15. The apparatus according to claim 14, wherein said antenna is connected to a frame area surrounding a closure member which is attached to said sterilization chamber, said closure member being constructed so as to recieve material to be sterilized.

16. The apparatus according to claim 14, wherein said antenna is firmly attached to said frame area.

17. The apparatus according to claim 14, wherein said monitoring means further comprises rectifier means for rectifying electrical signals received by said antenna, comparator means for comparing said rectified electrical signal to a threshold voltage and shut-off means for shutting off an electrical power supply to said microwave emitting devices upon said rectified electrical signal exceeding said threshold voltage.

18. The apparatus according to claim 17, further comprising alarm means for indicating that said rectified electrical signal exceeds said threshold voltage.

19. The apparatus according to claim 18, wherein said alarm means is constructed so as to provide a visual indication that said rectified electrical signal exceeds said threshold voltage.

20. The apparatus according to claim 18, wherein said alarm means is constructed so as to provide an audible indication that said rectified electrical signal exceeds said threshold voltage.

* * * * *